United States Patent [19]
Lundquist et al.

[11] Patent Number: 5,807,309
[45] Date of Patent: Sep. 15, 1998

[54] TRANSURETHRAL NEEDLE ABLATION DEVICE AND METHOD FOR THE TREATMENT OF THE PROSTATE

[75] Inventors: Ingemar H. Lundquist, Pebble Beach; Stuart D. Edwards, Los Altos; James A. Baker, Jr., Grass Valley; Christopher S. Jones, Palo Alto; Phillip R. Sommer, Newark; Kee S. Lee, Daly City, all of Calif.

[73] Assignee: Vidamed, Inc., Fremont, Calif.

[21] Appl. No.: 790,094

[22] Filed: Jan. 29, 1997

Related U.S. Application Data

[63] Continuation of Ser. No. 377,645, Jan. 25, 1995, Pat. No. 5,667,488, which is a continuation-in-part of Ser. No. 191,258, Feb. 2, 1994, Pat. No. 5,549,644, which is a continuation-in-part of Ser. No. 109,190, Aug. 19, 1993, Pat. No. 5,409,453, which is a continuation-in-part of Ser. No. 61,647, May 13, 1993, Pat. No. 5,421,819, and a continuation-in-part of Ser. No. 62,364, May 13, 1993, Pat. No. 5,435,805, which is a continuation-in-part of Ser. No. 12,370, Feb. 12, 1993, Pat. No. 5,370,675, which is a continuation-in-part of Ser. No. 929,638, Aug. 12, 1992.

[51] Int. Cl.⁶ .................................................. A61B 17/20
[52] U.S. Cl. ............................................... 604/22
[58] Field of Search ................................ 604/19–23, 53, 604/164, 280; 606/32, 39, 45; 601/2; 607/96, 113, 115, 116, 138, 156, 101, 102

[56] References Cited

U.S. PATENT DOCUMENTS

| | | |
|---|---|---|
| 2,008,526 | 7/1935 | Wappler et al. . |
| 2,038,393 | 4/1936 | Wappler . |
| 4,016,886 | 4/1977 | Doss et al. . |
| 4,474,174 | 10/1984 | Petruzzi . |
| 4,524,770 | 6/1985 | Orandi . |

FOREIGN PATENT DOCUMENTS 9315664  8/1993  WIPO .

OTHER PUBLICATIONS

Greenwald Surgical Company, Inc., "Orandi Resectoscope Injection Needle for Injection of Local Anesthetics," (Undated) Sheet No. P000121.

(List continued on next page.)

*Primary Examiner*—Michael Buiz
*Assistant Examiner*—Manuel Mendez
*Attorney, Agent, or Firm*—Flehr Hohbach Test Albritton & Herbert LLP

[57] ABSTRACT

A transurethral needle ablation device for use with the human hand for radio frequency ablation of a target volume in the tissue of a prostate of a human male having a bladder with a base and a penis with a urethra therein formed by a urethral wall extending into the base of the bladder along a longitudinal axis with the tissue of the prostate surrounding the urethra near the base of the bladder. The device comprises a bridge having proximal and distal extremities and having a passage therein extending from the proximal extremity to the distal extremity. A sheath having proximal and distal extremities is secured to the bridge and has a passageway therein in communication with the passage in the bridge. The sheath is sized so that it can enter the urethra and has a length so that when its distal extremity is in the vicinity of the prostate, the proximal extremity is outside the urethra. A disposable needle assembly having proximal and distal extremities is removably mounted in the passage in the bridge and extends through the passageway in the sheath. The needle assembly includes at least one needle electrode and an insulating sleeve coaxially disposed on the needle electrode. The proximal extremity of the needle assembly is caused to be moved sideways at an angle with respect to the longitudinal axis to face the urethral wall. A mechanism is carried by the proximal extremity of the needle assembly and the bridge for causing advancement of the needle electrode and the insulation sleeve thereon through the urethral wall and into the target volume in the tissue of the prostate with a portion of the electrode being free of the insulation but with the insulation extending through the urethral wall.

21 Claims, 5 Drawing Sheet

OTHER PUBLICATIONS

E.F. Nation, M.D., "Evolution of Knife–Punch Resectoscope," (Apr. 1976) Urology, vol. VII, No. 4, pp. 417–427.

R. Gutierrez, "Transurethral Treatment of Bladder Neck Obstructions: Endoscopic Prostatic Resection," (Apr. 1933) History of Urology, vol. II, Chapter V, pp. 137–186.

C.W. Ogden, Heat and the Prostate from Electrolysis to Microwaves: Lessons from an Historical Perspective, (Undated) Abstract, 2 sheets, p. 366.

Graversen, et al., "Transurethral incisions of the prostate under local anaesthesia in high–risk patients: a pilot study," (1987) Abstract, healthGate Home Page, p. P000115.

Miller, et al., "Integrated cystoscope: first rigid multipurpose operating cystoscope for local anesthetic endoscopy," (1989) Abstract, HealthGate Home Page, p. P000116.

Orandi, "Urological endoscopic surgery under local anesthesia: a cost–reducing idea," (1984) Abstract, healthGate Home Page, p. P000117.

Orandi, "Transurethral resection versus transurethral incision of the prostate," (1990) Abstract, HealthGate Home Page, p. P000118.

H. LeVeen, "Method for treating benign and malignant tumors utilizing radio frequency," (Nov. 16, 1976) Abstract, USPTO.GOV, U.S. Patent No. 3,991,770, pp. P000119–P000120.

R. Auhll, "The Use of the Resectoscope in Gynecology," (Oct. 1990) Biomedical Business International, pp. 91–99.

L. Geddes, "A Short History of the Electrical Stimulation of Excitable Tissue Including Electrotherapeutic Applications," (1984) A Supplement to The Physiologist, vol. 27, No. 1, pp. P000066–P000071.

W. Moseley, M.D., "The History of Treatment of BPH Including Current Treatment Alternatives," (Undated) pp. P000187–P000190.

D. Paulson, M.D., "Diseases of the Prostate," (1989) Clinical Symposia, vol. 41, No. 2., pp. P000191–P000195.

T. Kirwin, "The Treatment of Prostatic Hypertrophy by a New 'Shrinkage' Method," (Aug. 1934) J. Urology, pp: 481–494.

TRANSURETHRAL NEEDLE ABLATION DEVICE AND METHOD FOR THE TREATMENT OF THE PROSTATE

This is a continuation of abandoned application Ser. No. 08/377,645 filed Jan. 25, 1995, now U.S. Pat. No. 5,667,488, which is a continuation-in-part of application Ser. No. 08/191,258 filed on Feb. 2, 1994, now U.S. Pat. No. 5,549,644, which is a continuation-in-part of application Ser. No. 08/109,190 filed on Aug. 19, 1993 now U.S. Pat. No. 5,409,453 which is a continuation-in-part of applications 08/061,647 now U.S. Pat. No. 5,421,819 and 08/062,364 now U.S. Pat. No. 5,435,805 filed on May 13, 1993 which are continuations-in-part of application Ser. No. 08/012,370 filed on Feb. 2, 1993 now U.S. Pat. No. 5,370,675 which is a continuation-in-part of application Ser. No. 07/929,638 filed on Aug. 12, 1992, abandoned.

This invention relates to a transurethral needle ablation device and method for treatment of undesired conditions of a prostate in the human male and more particularly to such a device which utilizes a disposable needle assembly.

Benign prostatic hypertrophy or hyperplasia (BPH) is a common medical problem associated with aging men. Surgical procedures heretofore utilized to correct this problem have been expensive, time consuming and painful. In addition, such surgical procedures can have many undesirable side effects. There is therefore a need for a device and method which overcomes these disadvantages.

In general, it is an object of the present invention to provide a transurethral needle ablation device which can be utilized with a conventional cystoscope or urethroscope and a method which can be utilized for the treatment of undesired conditions of the prostate in the human male.

Another object of the invention is to provide a device and method of the above character in which a removable disposable needle assembly is provided in a reusable bridge and which can be disposed of after a one-time use in the treatment of the human male.

Another object of the invention is to provide a device and method of the above character in which tenting of the urethral wall is minimized.

Another objection of the invention is to provide a device and method of the above character in which the needle is introduced with rapidity to minimize tenting of the urethral wall during insertion of the needle.

Another object of the invention is to provide a device and method of character in which a tragic release mechanism is utilized and for introducing the needle electrode through the urethral wall and into the tissue of the prostate.

Another object of the invention is to provide a device and method of the above character in which yieldable means is used for moving the needle electrode through the urethral wall.

Another object of the invention is to provide a device and method of the above character which utilizes radio frequency energy for ablation.

Another object of the invention is to provide a device and method of the above character in which the urethral wall is protected from radio frequency ablation during the time that radio frequency ablation is occurring in the prostate.

Another object of the invention is to provide a device and method of the above character in which the needle serving as a radio frequency electrode is provided with insulation to insulate the needle electrode from the probe of the urethroscope.

Another object of the invention is to provide a device and method of the above character in which the insulation sleeve for the needle electrode remains fixed with respect to the needle electrode to expose a predetermined portion of the needle electrode for use in radio frequency ablation.

Another object of the invention is to provide a device and method of the above character in which the insulation sleeve is movable relative to the needle electrode so that various lengths of the needle electrode can be exposed for radio frequency ablation.

Another object of the invention is to provide a device and method of the above character in which the length of needle electrode exposed beyond the insulation can be preadjusted.

Another object of the invention is to provide a device and method of the above character in which the needle electrode can be advanced after the insulation sleeve has been advanced through the urethral wall.

Another object of the invention is to provide a device and method of the above character in which the temperature of the distal extremity of insulating sleeve is measured.

Another object of the invention is to provide a device and method of the above character in which the patient can be treated without the use of anesthesia except for possibly a local anesthetic.

Another object of the invention is to provide a device and method wherein two needle electrodes can be introduced at the same time to penetrate the urethral wall and enter into the prostatic tissue.

Another object of the invention is to provide a device and method of the above character in which the needle electrodes can be readily redeployed without removal of the device to create an additional set of lesions in the prostate.

Another object of the invention is to provide a device of the above character which the needle assembly is relatively lightweight and inexpensive.

Additional features of the invention will appear from the following description in which the prepared embodiments are set forth in detail with the company drawings.

In general, the transurethral needle ablation device is for use with the human hand for radio frequency ablation of a target volume in the tissue of a prostate of a human male having a bladder with a base and a penis with a urethra therein formed by a urethral wall extending into the base of the bladder along a longitudinal axis with the tissue of the prostrate surrounding the urethra near the base of the bladder. The device is comprised of an elongate member having a proximal and distal extremities and having a longitudinal axis and being sized so as to be able to enter the urethra and having a length so that when the distal extremity of the elongate member is disposed in the vicinity of the prostate the proximal extremity of the elongate member is outside the urethra. The elongate member has a side wall defining a passageway extending along the longitudinal axis. The distal extremity has an outlet port in communication with the passageway. A radio frequency electrode of an electrically conductive material is disposed in the passageway and has a sharpened tip. A sleeve of insulating material is coaxially mounted on the radio frequency electrode and is also disposed in the passageway. The sleeve is disposed on the radio frequency electrode so that a preselected length of the radio frequency electrode extends beyond the sleeve and is exposed in the target volume of the prostate when the radio frequency electrode has been advanced into the target volume. The tissue of the prostate in the target volume surrounds the preselected length of the radio frequency electrode. Means is provided for supplying radio frequency energy the radio frequency electrode for causing ablation of the target volume.

More in particular as shown in FIGS. 1 through 11 of the drawings, the transurethral needle ablation device 21 of the present invention consists of a bridge assembly 22 which has removably mounted thereon a sheath assembly 23 which is adapted to receive a conventional cystoscope or urethroscope 24 which extends through the bridge assembly 22 and through the sheath assembly 23. A disposable removable needle assembly 26 which also can be characterized as a disposable removable cartridge assembly is removably seated within the bridge assembly 22 and extends through the sheath assembly 23.

The bridge assembly 22 consists of a bridge housing 31. The bridge housing 31 can be formed by the suitable materials such as a polycarbonate and can be formed in two parts if desired to facilitate assembly. The bridge housing 31 has been contoured so as to particularly adapted to fit with any human hand and is provided with forwardly facing curved recess 36 that is adapted to be engaged of by the index finger of the human hand with the remainder of the housing being adapted to be engaged by the palm of the hand.

Figures 1, 2, 3, 4:
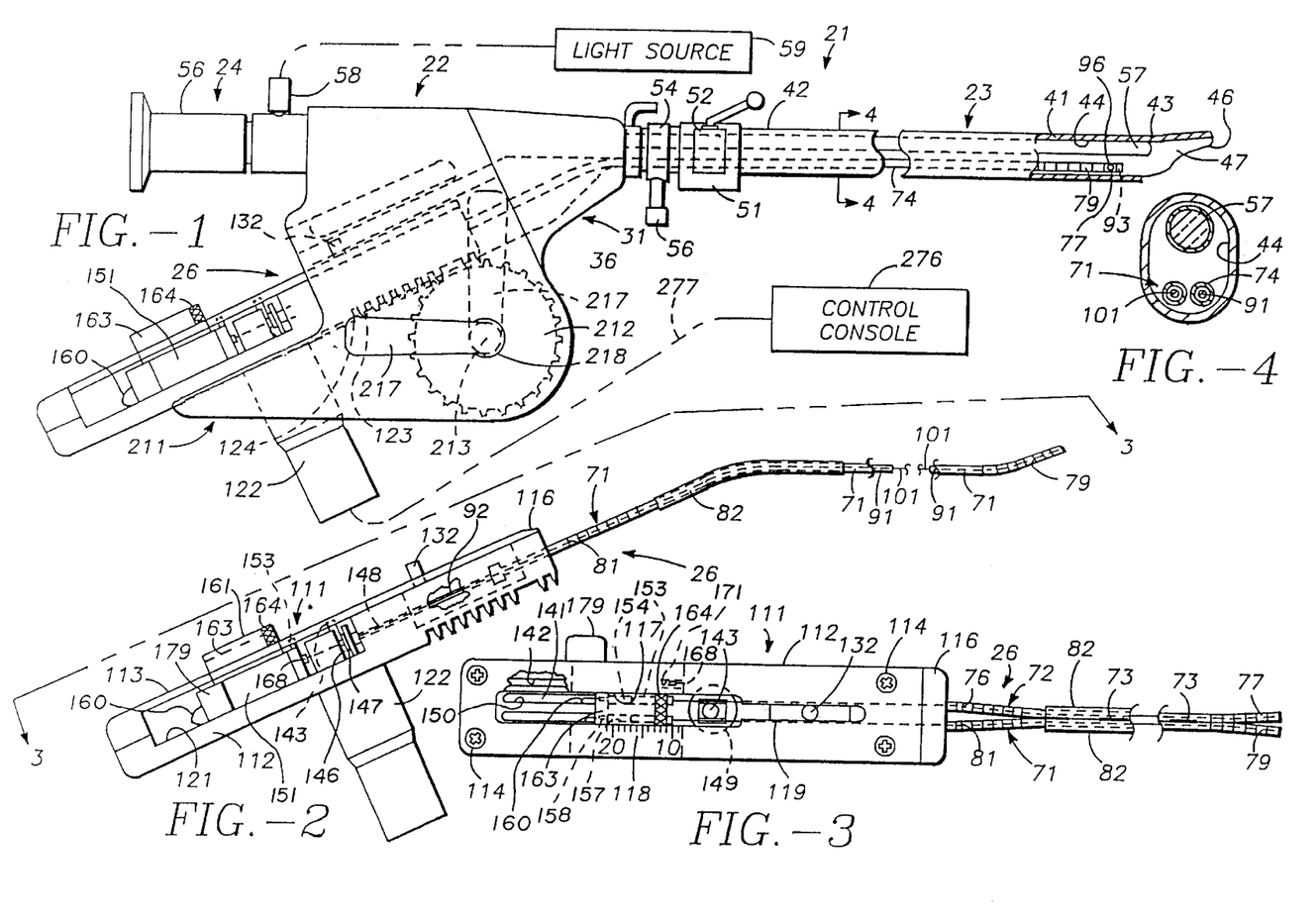
FIG. 1 is a side elevational view of a transurethral needle ablation device incorporating the present invention with a removable disposable needle assembly disposed therein.
FIG. 2 is a side elevational view of the needle assembly shown in FIG. 1.
FIG. 3 is a view of the needle assembly shown in FIG. 2 looking along the line 3—3 of FIG. 2.
FIG. 4 is a cross sectional view taken along the line 4—4 of FIG. 1.

The sheath assembly 23 includes a rigid sheath 41 of a suitable size as 21 French to serve as a rigid catheter-like delivery device having a suitable length as for example 25 centimeters. The sheath 41 is formed of a suitable material such as stainless steel and is provided with a proximal and distal extremities 42 and 43 with an oval-shaped bore or lumen 44 extending from the proximal extremity 42 to the distal extremity 43. As shown particularly in FIG. 1, distal extremity 43 is provided with a forwardly and upwardly extending curved surface 46 through which an upwardly inclined opening 47 extends and which is in communication with the lumen bore 44. The sheath assembly 23 includes a hub 51 mounted on the proximal extremity 42 of the sheath. The hub 51 carries first and second stop cocks 52 on opposite sides of the same A locking ring 54 is rotatably mounted on the hub 51 and is provided with a handle 56 for locking the sheath assembly 23 onto the frontal extremity of the bridge housing 31 as shown in FIG. 1.

The cystoscope 24 is mounted on the bridge assembly 22 and which is adapted to extend into the sheath assembly 23. It is of a conventional type and is a direct vision cystoscope. It is provided with an eye piece 56 attached to an optical tube 57 which is adapted to be seated in the bridge assembly 27 as hereinafter described and extend into the sheath 41 of the sheath assembly 23. The optical tube 57 is of a conventional type and contains a plurality of rod-like optical elements (not shown) to provide excellent viewing capabilities at the distal extremity of the optical tube 57. The optical tube 57 is provided with a 0° viewing angle so that it can view the region immediately in front of the same adjacent the distal extremity 43 of the sheath 41 for purposes herein after described. The optical tube 57 is provided with a fitting 58 which adapted be connected to a suitable source of light as for example the light source 59 shown in FIG. 1.

The needle cartridge assembly 26 which removably mounted in the bridge assembly 22 consists of first and second guide tube assemblies 71 and 72 which are slidably mounted in the passage way or bore 44 of the rigid sheath 41. The guide tube assemblies 71 and 72 are substantially identical to each other and as shown in FIG. 3 are mounted side by side and are fastened together by suitable means such as solder connections 73.

Each of the guide tube assemblies 71 and 72 consists of an outer guide tube 74 (see FIG. 4) formed of a suitable material such as stainless steel having a 15 gauge wall thickness with an outside diameter of 0.072 inches and an inside diameter of 0.060 inches. The outer guide tube 74 is provided with proximal and distal extremities 76 and 77. The proximal extremity 76 is provided with the flange 78 (see FIG. 9). As described in copending application Ser. No. 08/191,258 filed on Feb. 2, 1994, the distal extremity 77 is provided with a plurality of longitudinally spaced apart circumferential extending L-shaped slots 79 as for example the last 1.5 centimeters of the guide tube 74. The slots 79 subtend less than 360° and have a suitable width as for example 0.012" and are spaced apart a suitable distance as for example 0.033". The slots 79 are L-shaped and are provided with a toe or short leg length portion having a length of 0.010". The slots 79 are not angularly offset and therefore provide a backbone or rib (not shown) extending longitudinally of the outer guide tube 74. The proximal extremity 76 of each outer guide tube 74 is provided with a plurality of longitudinally spaced apart slots 81 (see FIG. 2). The slots 81 can have a suitable width as for example 0.023 to 0.025" and can be spaced apart a suitable distance as for example 0.04". The slots 81 subtend an angle less than 360° and by way of example can subtend an angle of 270° and be rotated by 120° with respect to each other. The slots 81 extend over the suitable distance as for example 1.2 to 1.5" whereas the slots 79 can extend over a distance of approximately 0.5".

A sleeve 82 formed of a heat shrinkable plastic is disposed over both guide tube assemblies 71 and 72 commencing at the distal extremity of the slots 81 and extending for approximately one inch there beyond. This sleeve 82 facilitates movement of the needle assembly into the bridge assembly 22 as hereinafter described.

A pull element or pull ribbon 86 having a proximal extremity (see FIGS. 11 and 12) is provided within each of the outer guide tubes 74 and is secured to the distal extremity in a manner as disclosed in copending application Ser. No. 08/191,258. Each of the guide tube assemblies 71 and 72 includes an insulation tube 91 of the type described in copending application Ser. No. 08/191,258 filed on Feb. 2, 1994. The insulation tube 91 is slidably mounted in the outer guide tube 44 and is provided with proximal and distal extremities 92 and 93. A thermocouple 96 is mounted in the distal extremity 93 of the insulation tube 91 in the manner described in copending application Ser. No. 08/191,258 and is coupled by conductors 97 extending to the proximal extremity within the guide tube 74.

A needle electrode 101 is slidably mounted in the insulation tube 91 and also is of the type described in the copending application Ser. No. 08/191,258 filed on Feb. 2, 1994. As therein described, the needle electrode 101 is formed of a suitable material such as a nickel titanium alloy having superelastic properties so that it will return to its original configuration after being bent. It is provided with a proximal extremity 102 and a distal extremity 103 in the form of a sharp needle-like point.

A housing or cartridge 111 is mounted on the proximal extremities of the guide tube assemblies 71 and 72 and forms a part of the needle cartridge assembly 26. The housing or cartridge 111 consists of a body 112 which is rectangular in cross section and has a suitable width as for example ½" and a length of approximately 2½". The cartridge or housing 111 also consists of a cover plate 113 which is secured to the body 112 by suitable means such as screws 114. The forward or distal extremity of the cover plate 113 is provided with a chamfer 116 to facilitate the introduction of the cartridge 111 into the bridge assembly 22 as hereinafter described. The cover plate 113 is provided with an elongate slot 117 which has a scale of 118 shown in millimeters (see FIG. 3) disposed on one side of the slot 117 and is utilized for a purpose hereinafter described. U-shaped cutouts 121 are provided in opposite sides of the body 112 (see FIG. 2) for a purpose hereinafter described. An electrode connector 122 is mounted on the body 112 and extends downwardly therefrom (see FIG. 9).

The proximal extremities of the guide tube assemblies 71 and 72 are disposed of within transversely spaced apart parallel slots 126 in the body 112 (see FIG. 7) and are clamped into place by a square brass plate 127 clamped into place by a screw 128.

The lowermost distal extremity of the body 112 is provided with the plurality of a downwardly extending transversely disposed teeth 123 which form a stationary rack 124. As it can be seen, this rack 123 is provided with a space 125 in which one tooth is missing for a reason hereinafter described.

An additional rectangular plate 131 (see FIG. 12) formed of a suitable material such as stainless steel is seated over the guide tube assemblies 71 and 72 and serves to hold them in place. The plate 131 is clamped into place by the cover plate 113 secured to the body 112 by the screws 114. The plate 131 is provided with a centrally disposed upwardly extending one-way breakoff pin 132 which extends through the slot 119 provided in the cover plate 113. The breakoff pin 132 is provided with a recess 132a extending partially therethrough in a direction perpendicular to the axis of the pin 132 to permit the pin 132 to break off when it is pulled against the shoulders hereinafter described. The pin 132 is formed of a metal such as brass which has good tensile strength and is formed of a relative hard material so that it is brittle and will break off when the cartridge assembly or needle assembly 26 is withdrawn after use to prevent reuse of the cartridge assembly 26 as hereinafter described. The breakoff pin 132 is mounted in the plate 131 by suitable means such as a press fit. The plate 131 is provided with a recess 133 (see FIG. 12) which is adapted to frictionally receive a wedge 134 that is provided with a wedging surface 135 having a suitable angle as for example 5° which frictionally engages the proximal extremities of the pull ribbons 86 to frictionally clamp the same between the wedge 134 and the surface of the plate 131 forming the recess 133. The wedge 134 and the plate 131 are formed of a suitable material such as stainless steel.

The plate 131 is provided with a pair of horizontally aligned bores 136 with which align with a corresponding pair of aligned bores 137 in the wedge 134. The outer guide tubes 74 of the guide tube assemblies 71 and 72 have outwardly flared ends 138 on the proximal extremities 76 seated within the bores 136 and having the flared ends 138 retained in an annular recesses 139 provided in the plate 131 just slightly distal of the recess 133 in the plate 131. The insulation tubes 91 with the needle electrodes 101 therein extend proximally through the bores 137 in the wedge 134.

An insulation actuator 141 formed of a suitable plastic material such as a black polycarbonate is slidably mounted in a recess 142 provided in the body 112. The actuator 141 is provided with an upstanding pin 143 which extends upwardly through the slot 117 in the cover plate 113. The insulator actuator 141 is also provided with a pair of arcuate recesses 146 which are adapted to receive the flanged proximal extremities 147 of the stainless steel hypotubes 148 which form a part of the proximal extremity of the insulation tube 91 described in copending application Ser. No. 08/191,258 filed on Feb. 2, 1994. Thus it can be seen that the proximal extremities of the insulation tubes 91 are fixed in insulation actuator 141 which is slidably mounted within the body 112. The needle electrodes 101 extend proximal from the insulation tubes 91. The thermocouple conductors or wires 97 connected to the thermocouples 96 also extend to the proximal extremity of the insulation tubes 91 and extend downwardly into the cable connector sleeve 122. The length of the thermocouple wires 97 is sufficient to permit rectilinear movement of the insulator actuator 141 within a hole 149 provided in the body 112. A pair of spaced-apart elongate slots 150 extend longitudinally of the insulator actuator 141 and are used for the purpose hereinafter described.

A needle actuator 151 is slidably mounted within the cartridge 111 and is slidably mounted on the insulation actuator 141. The needle actuator 141 is formed of a suitable plastic such as a clear polycarbonate to provide a color differentiation between the needle actuator 151 and the black carbonate forming the body 112 and the cover plate 113 in which the needle actuator travels. The needle actuator 151 is provided with a pair of threaded aligned bores 152. Screw members 153 are provided with enlarged cylindrical portion 154 which are adapted to seat against annular shoulders 156 provided in the needle actuator 151. The enlarged cylindrical portion 154 is provided with a slot 157 which can be used in conjunction with the tool (not shown) for adjustably positioning the screw member 153 in the bore 152. The screw members 153 are also provided with thin wall cylindrical extensions 158 having bores 159 extending therethrough and extending through the enlarged cylindrical portions 154. The needle electrodes 101 extend through the bores 159 and have therein proximal extremities frictionally clamped within the cylindrical extension 158 by crimping the cylindrical extension 158 therein. It can be seen by rotating the screw members 153 within the threaded bores 152, the longitudinal positions of the needle electrodes 101 relative to the insulation tubes 91 may be adjusted for purposes hereinafter described. The cylindrical extension 158 is connected to insulated leads 160 that are soldered thereto and extend through the slots 150 in the insulator actuator and through the hole 149 in the electrical connector 122.

The needle actuator 151 is provided with an upstanding protrusion 161 (see FIG. 9) which extends upwardly through the slot 117 and is provided with a threaded bore 162 therein which lies in a plane parallel to the plane of the cover 113. An adjustment screw 163 having a knurled knob 164 on the same is threaded into the threaded bore 163. The knob 164 is adapted to engage the upstanding pin 143 extending upwardly through the slot 117 as hereinafter described.

The needle actuator 151 is provided with a spring finger 166 which is formed integral with the needle actuator and which is provided by a slot 167 formed in the needle actuator. The spring finger 166 is provided with an upstanding portion 168 which carries an outwardly extending portion 169. The portion 169 is yieldably urged outwardly by the spring finger 166 and is adapted to releasably seat in a rectangular recess 171 provided in the cover plate 113.

A pin 176 formed of a suitable material such as plastic is mounted on the spring finger 166 and extends outwardly therefrom. The pin 176 is provided with an outwardly extending flange 177. A knob 179 which is generally rectangular in cross section is rotatably mounted on the pin 176 and has a bore 181 therein which is adapted to fit over the pin 176. A shoulder 182 is provided within the bore and is adapted to be pushed over and engage the flange 177 provided on the pin 176. The knob 179 because it is rectangular in cross section (see FIG. 9) has a narrower dimension which is slightly less than the width of the slot 121 provided in the body 112 so that when the outwardly extending portion 129 is released from the recess 179, the needle actuator 151 can be advanced within the body 112 as hereinafter described. The knob 179 has a dimension in the other direction of its rectangular cross section which is greater than the width of the slot 121 so that when the knob is rotated by 90° it cannot be pushed inwardly because it has portions which extend beyond the slot 121 and thereby preventing release of the protrusion or outwardly extending portion 169 of the spring finger 166.

Figures 7, 8, 9, 10, 11, 12:
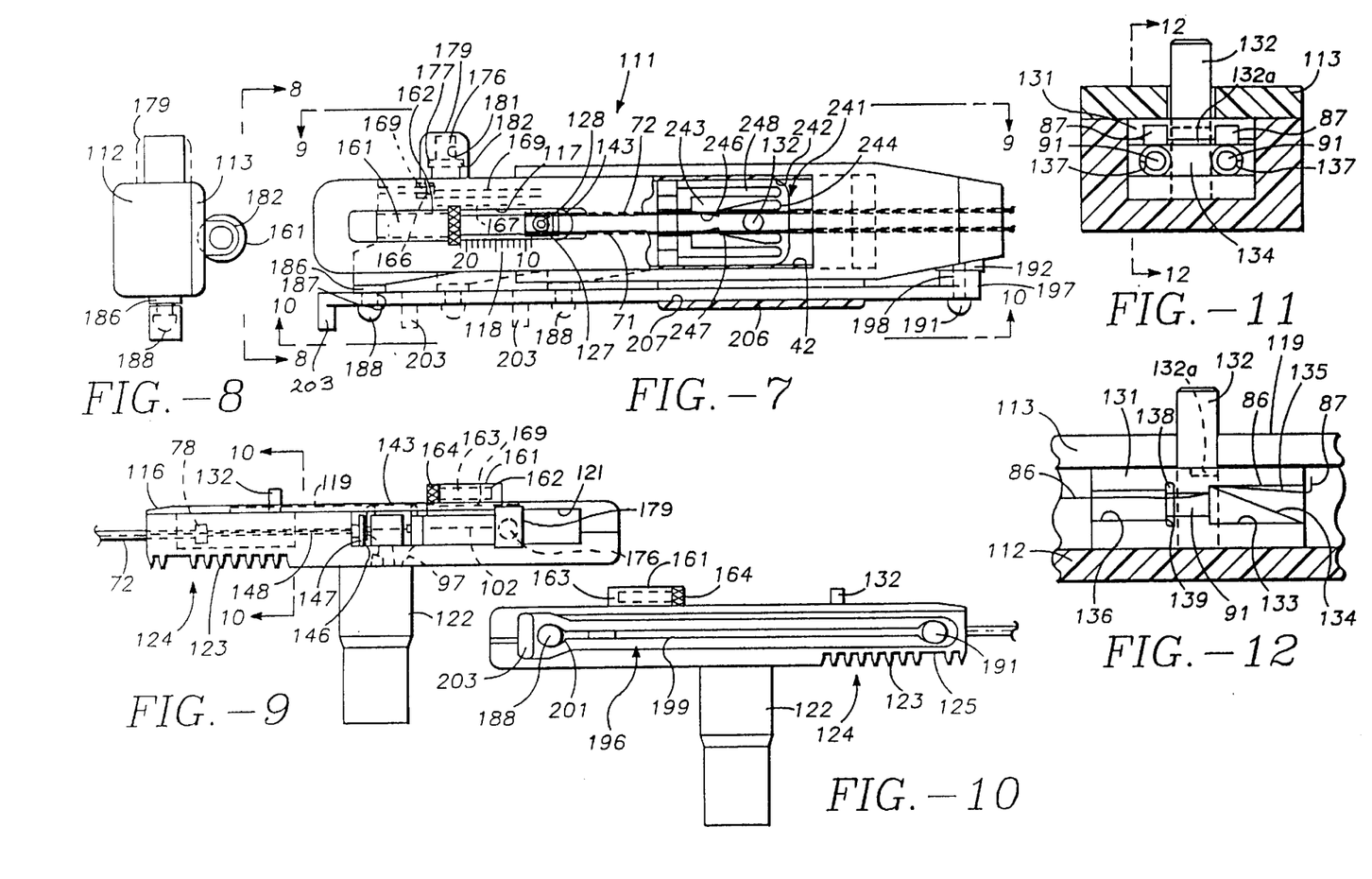
FIG. 7 is an enlarged plan view of the proximal extremity of the needle assembly shown in FIG. 3.
FIG. 8 is an elevational view taken along the lines 8—8 of FIG. 7.
FIG. 9 is a reduced side elevational view taken along the line 9—9 of FIG. 7.
FIG. 10 is a reduced side elevational view taken along the line 10—10 of FIG. 7.
FIG. 11 is a cross sectional view taken along the line 11—11 of FIG. 9.
FIG. 12 is a cross-sectional view taken along the line 12—12 of FIG. 10.

A pin 186 (see FIG. 8) is mounted on the needle actuator 151 on the side opposite the spring finger 166. It extends outwardly through the cutout 121 provided on the opposite side of the body 112. The pin 186 is provided with an annular recess 187 and has a rounded conical protrusion 188. An outwardly extending pin 191 is provided on a boss 192 on the body 112. Yieldable elastic means 196 in the form of a latex rubber band 196 has an inwardly extending protrusion 197 therein which is provided with a bore 198 permitting the protrusion to be fitted over the pin 191 (see FIG. 7). The rubber band 196 is provided with an elongate slot 199 which opens into a larger opening 201 which receives the pin 186 and permits the rubber band 196 to seat within the annular recess 187. The proximal end of the rubber band 196 is provided with an outwardly extending protrusion 203 which is adapted to be engaged by two fingers of the human hand to facilitate loading of the rubber band 196 onto the pin 186. The pin 186 as shown in FIG. 7 is in the loaded position with other positions of the pin 186 being shown in dotted lines for the "operating" position and the "fired" position, respectively, looking from left to right in FIG. 7. A U-shaped enclosure 206 (see FIG. 7) is secured to the side of the body 112 and is provided with a U-shaped recess 207 in which the rubber band 196 is disposed.

The bridge assembly 22 consists of a housing 211 formed of a suitable material such as black polycarbonate. If desired, the housing 211 can be formed of two parts which can be fastened together by suitable means such as screws or ultrasonic bonding. A large spur gear 212 is rotatably mounted within the housing 211 and is fixed to a shaft 213 by a screw 214 engaging a flat 215. The shaft 213 extends through holes (not shown) provided in opposite sides of the housing 211 and has a rectangular knob 217 mounted thereon on one side of the housing 211 and secured thereto by suitable means such as a screw 218.

Means is provided for limiting rotation of the spur gear 212 between a limited angle, as for example an angle of 90°, and consists of a pin 221 carried by the housing 211 which extends through an arcuate slot 222 provided in the spur gear 212.

Means is provided for yieldably retaining the spur gear 212 in various positions as determined by the spacing of the teeth 226 of the spur gear 212 and consists of a roller pin 227 (see FIG. 5) mounted in a recess 228 in the housing 211 and yieldably urged into recesses between the gear teeth 276 and into engagement with the gear teeth 226 by a rectangular rubber member 229 disposed in a slot 231 in the housing 211 and yieldably urging the roller pin 227 in a direction toward the teeth 226 of the spur gear 212. A spring metal reinforcing strip 232 is placed in front of the rubber member 229 and engages the pin 227.

Figures 5, 6, 13:
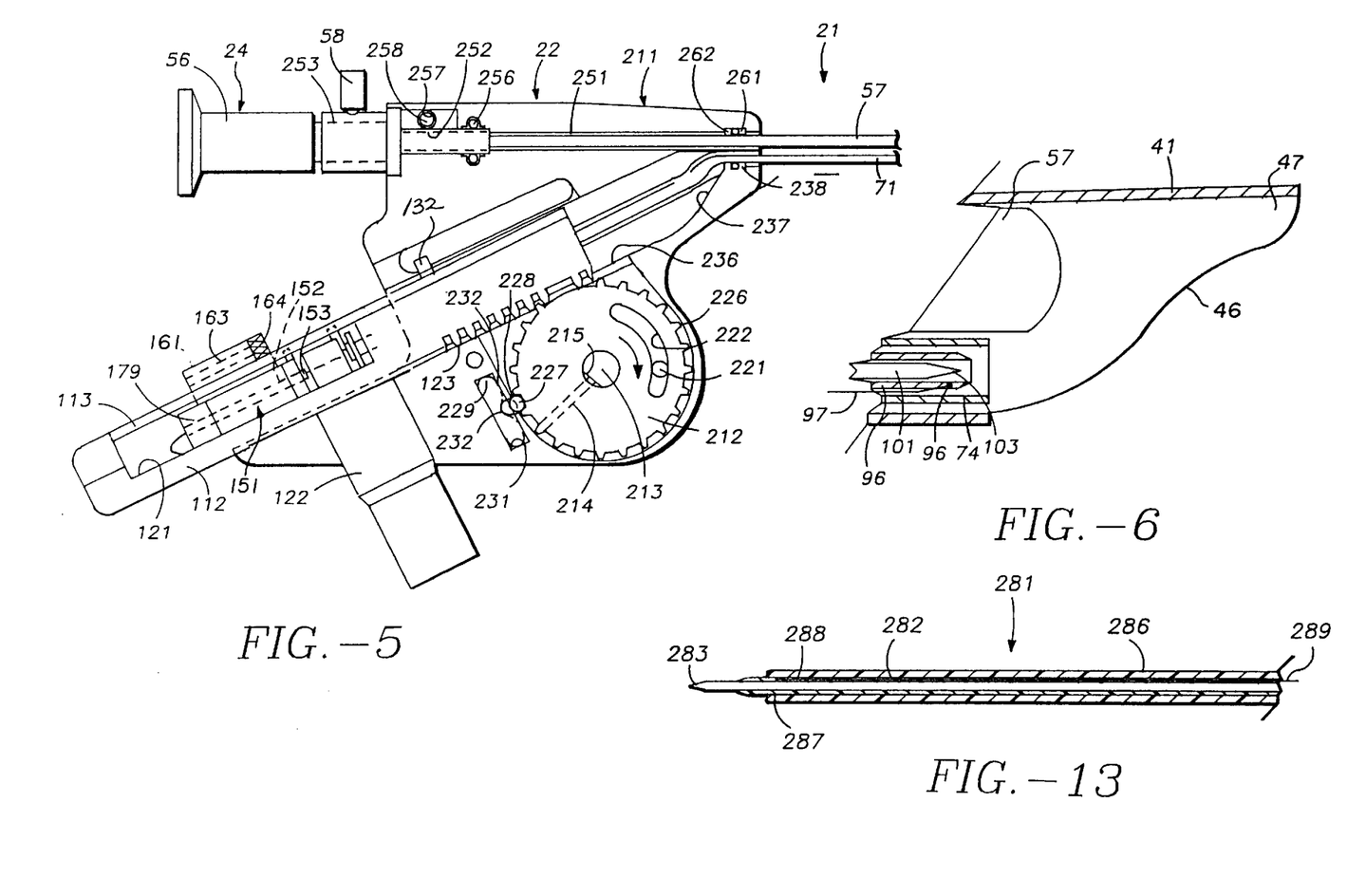
FIG. 5 is an enlarged side elevational view of a portion of the device shown in FIG. 1 and particularly the bridge assembly with certain portions broken away.
FIG. 6 is an enlarged cross-sectional view of the distal extremity of the device shown in FIG. 1.
FIG. 13 is a side elevational view in section of another embodiment of a transurethral needle ablation device having a fixed insulation sleeve.

As shown particularly in FIG. 5, one of the teeth 226 of the spur gear 213 is missing to permit entry of the stationary rack 124 carried by the body 112 when the cartridge 111 is introduced into a rectangular recess 236 provided in the body which opens distally into a tapered passageway 237. The tapered passageway 237 opens into an oval shaped passageway 238 through which the guide tube assemblies 71 and 72 are adapted to extend.

Means is provided in the housing 211 for receiving the breakoff pin 132 and consists of a spring clip 241 (see FIG. 7) formed of a suitable material such as stainless steel which is seated within a recess 42 provided in the housing 211. The spring clip 241 is provided with two proximally extending spring fingers 243 carried by a base 244. The spring fingers 243 are spaced apart and parallel and are provided with cam surfaces 246 which are adapted to be engaged by the breakoff pin 132 as the cartridge 111 is advanced into the recess 236. The fingers 243 face proximally into a recess 248 in the housing 211 which is adapted to receive the breakoff pin 132. As the cartridge 111 continues to be advanced, the teeth 226 on the spur gear 212 engage the rack teeth 123 carried by the cartridge. The one-way breakoff pin 132 during this movement of the cartridge 111 cams the fingers 243 outwardly from each other until the breakoff pin 132 clears the camming surfaces 246 permitting the spring fingers 243 to snap back into their normal positions but preventing the breakoff pin from re-exiting through the fingers 243 because of engagement with shoulders 247 provided on the fingers 243.

The bridge assembly 22 also includes a bore 251 (see FIG. 5) which receives the optical tube 57 of the cystoscope 24. The bore 251 opens proximally into a larger bore 252 which opens into a still larger bore 253 provided in the housing adapted to receive the cystoscope 24. An O-ring 256 is mounted in the housing and forms a fluid-tight seal with the cystoscope 24. The housing 211 is also provided with a small hole 257 overlying the bore 252 which is adapted to receive a registration pin 258 carried by the cystoscope 24.

Another O-ring 261 is mounted within the housing 211 and is seated within an annular recess 262 provided in the housing 211. The O-ring 261 releasably engages the optical tube 57 of the cystoscope 24 and also releasably engages the guide tube assemblies 71 and 72 to form a fluid-tight seal therewith.

Operation and use of the transurethral needle ablation device 21 of the present invention and the method for using the same for treatment of the prostate may now be briefly described as follows. Let it be assumed that the physician has previously examined the prostate with a conventional cystoscope or urethroscope and has determined that the patient has an enlarged prostate which requires treatment by use of RF ablation by utilizing the device and method of the present invention. Since the bridge assembly 22 is a reusable device, let it be assumed that the bridge assembly 22 has been properly sterilized as has the sheath assembly 23 and that the sheath assembly 23 has been mounted on the bridge assembly 22. A conventional cystoscope 24 is inserted into the bridge assembly 22. The fitting 58 is connected to a conventional light source 59 (see FIG. 1).

The physician next removes a disposable needle cartridge assembly 26 from the packaging as shipped by the manufacturer. The physician adjusts the knob 164 using the scale 118 and determines the amount that the needle electrode 101 is to extend beyond the insulation tube 91 during an ablation procedure. By way of example let it be assumed that the physician has determined that a needle length of 7 millimeters is appropriate. The knob 164 of the needle adjustment screw 163 is then adjusted with respect to the scale 118 so that the knob is in registration with the 7 millimeter dimension of the scale 118.

The trigger mechanism consisting of yieldable elastic means 196 is then set or cocked by pulling rearwardly or proximally on the protrusion 203 until the outwardly extending portion 169 snaps into the recess 171 and rotating the knob 179 so that it is in a vertical position preventing it from being depressed into the cut-out 121. The needle cartridge assembly 26 can then be connected to a suitable source of radiofrequency energy, as for example a control console 276 of a type well known to one skilled in the art by suitable cabling 277 to the connector sleeve 122.

The needle cartridge assembly 26 can then be inserted into the bridge assembly 22 by inserting the guide tube assemblies 71 and 72 through the rectangular recess 236 and then into the tapered passageway 237 and into the oval-shaped passageway 238 past the O-ring 262 and into the sheath assembly 23 followed by the cartridge 111. The cartridge 111 is advanced until the forward extremity of the cartridge is disposed in the space in which the tooth 226 is missing.

The assembled device 21 is now ready for use. In the meantime, the patient has been prepared by having the urethra in the penis filled with an antiseptic gel. The rigid sheath 41 is then introduced into the urethra under view through the eye piece 56 and advanced into the urethra until the distal extremity of the rigid sheath 41 is disposed within the bladder of the patient. During the time that the rigid sheath 41 is being introduced into the urethra, a saline solution is introduced into the urethra simultaneously so that the antiseptic gel which is water soluble is washed away and a clean field of view of provided in front of the optical tube 51 of the cystoscope 24 so that the physician can view the progress of the rigid sheath 41 as it is being introduced into the urethra. After the physician has ascertained the anatomical construction of the urethra and the commencement of the sphincter muscle from the bladder, the physician withdraws the rigid sheath 41 until the physician is sure that the distal extremity of the sheath is disposed within the patient's prostate that surrounds the urethra immediately proximal of the bladder. The physician then rotates the bridge assembly 22 using one hand to grasp the housing 111 to rotate the rigid sheath 41 until the distal extremity is disposed at the proper angle within the prostate so that radiofrequency ablation can be carried out in the desired lobe of the prostate. As soon as this has been ascertained, the physician uses the other hand to grasp the knob 217 to move it from a horizontal position to a generally vertical position to thereby cause the spur gear 212 to rotate in a clockwise position as viewed in FIG. 5 to cause the teeth 216 thereon to engage the teeth 123 of the stationary rack on the cartridge 111 to move the cartridge 111 forwardly.

As the housing 111 is moved forwardly into the rectangular recess 236, the one-way breakoff pin 132 is advanced between the camming surfaces 246 to spread apart the spring fingers 243. This movement continues until the cam surfaces 246 are cleared permitting the spring fingers 243 to snap into their normal positions and to hold the breakoff 132 pin in place so that it cannot be retracted without breaking off the breakoff pin.

As the housing 111 is advanced, the pull ribbons 86 are pulled to cause the outer distal extremities of the guide tube assemblies 71 and 72 to be bent so that they extend essentially at right angles with respect to the longitudinal axis of the sheath 41 by engagement of the breakoff pin 132 carried by the plate 131 with the bridge housing 211. As the distal extremities of the guide tube assemblies 71 and 72 are being deployed at a suitable orientation, as for example at an 85° angle with respect to the longitudinal axis of the sheath 41 separated at a suitable angle, as for example 30° as disclosed in co-pending application Ser. No. 08/191,258 filed Feb. 2, 1994. The physician by looking through the cystoscope 24 can observe this deployment. As soon as the physician has ascertained that the distal extremities of the needle assembly 71 and 72 are deployed in the proper directions, the physician can release the trigger mechanism hereinbefore described by rotating the knob 179 through 90° so that its longer face lies in horizontal plane parallel with the plane of the cutouts 121. Pushing inwardly on the knob 179 causes the spring finger 166 to be depressed to cause the outwardly extending portion 169 to be released from the recess 171 permitting the needle actuator 151 to be urged forwardly causing the needle electrodes 101 carried thereby to be rapidly urged through the urethral wall so that tenting of the urethral wall is minimized and then advanced into the prostate for the predetermined distance set by the knob 164. As hereinbefore described, the knob 164 was set for a distance of 7 millimeters, which means that the needle electrodes 101 will be advanced by that distance until the knob 164 strikes the upstanding pin 143 to thereafter carry with it the insulation actuator 141. The needle actuator 141 and the insulation actuator 141 then move in unison for another predetermined distance, which for example can be set for a distance ranging from 5 to 8 millimeters and preferably a distance of 6–7 millimeters. The insulation tubes 91 are also rapidly urged through the urethral wall and extend through the urethral wall for a distance of approximately 6 to 7 millimeters with the needle electrodes being further advanced by the same amount so that the distal extremities of the needle electrode exposed outside of the insulation tube are exposed for a distance of approximately 7 millimeters.

In the present embodiment of the invention, it can be seen that the needle electrodes 101 are first moved into the prostate and are followed by the insulation tubes 91. After the needle electrodes 101 and the insulation tubes 91 have been appropriately positioned, radiofrequency energy is applied from the control console 276 to the radiofrequency electrodes for an appropriate period of time as for example 2 to 5 minutes. Radiofrequency ablation is carried out in the manner described in co-pending application Ser. No. 08/191, 258 filed Feb. 2, 1994 so that the urethral wall is at all times protected from radiofrequency ablation. This is accomplished by having insulation tubes 91 extend a suitable distance into the prostate, as for example the 7 millimeters hereinbefore described, to ensure that a protected region is provided in the prostate immediately adjacent the urethral wall to protect the urethral wall.

After radiofrequency ablation of the prostrate has been completed, the knob 179 is grasped and retracted to bring back with it the needle actuator 151. Movement of the needle actuator 151 causes the needle electrodes 101 to be retracted until their distal extremities are retracted slightly within the distal extremity of the insulation tubes 91 as for example 0.010". Thereafter continued retraction of the needle actuator 151 causes the insulation actuator 41 to follow and to move it back to the load position hereinbefore described. Thereafter, the distal extremities of the guide tube assemblies 71 and 72 are straightened by returning the knob 217 to a horizontal position from the dotted line position shown in FIG. 1.

Now let it be assumed that it is desired to perform radiofrequency ablation in the other lobe of the prostate. The physician, after retraction of the needle actuator 151 and insulation actuator 151 and straightening of the distal extremity of the guide tube assemblies 71 and 72, can rotate the rigid sheath 41 by a suitable angle as for example 60° after which the same procedure can be completed. First, the knob 217 is rotated until it is in the horizontal position causing the distal extremities of the guide tube assemblies 71 and 72 to extend at substantially right angle directions with respect to the longitudinal axis of the rigid sheath 41. Thereafter, the knob 179 can be rotated so that its long surface is parallel to the cutout 121. It can then be depressed to release the outstanding abutment 169 from the recess 171 to release the trigger mechanism in the form of yieldable elastic means 196 to again rapidly move the needle electrodes 101 forwardly for a predetermined distance followed by the insulation tubes 91 also for a predetermined distance so that the needle electrodes 101 and the insulation tubes 91 are disposed within the other lobe of the prostate with insulation tubes 91 being disposed inwardly sufficiently to protect the urethral wall during radiofrequency ablation. Thereafter radiofrequency energy is applied to the needle electrodes 101 to provide the desired radiofrequency ablation of the prostate.

After this second procedure has been completed, if desired the device 21 can be removed first by grasping the knob 179 and retracting the needle electrodes 101 followed by the insulation tubes 96 into the outer guide tubes 74 with the needle electrodes 101 always extending for a slight distance beyond the distal extremity of the insulation tubes 91. Thereafter, the distal extremities of the guide tube assemblies 71 and 72 can be straightened by bringing the knob 217 back to a horizontal position. Thereafter, the entire device 21 can be removed from the urethra. The needle cartridge assembly 26 can be removed from the bridge assembly 22 by pulling the cartridge forwardly to bring the breakoff pin 132 into engagement with the shoulders 247 to cause the same to break off. The needle cartridge assembly 26 can then be disposed of. Since the breakoff pin has been broken off, the needle cartridge assembly 26 cannot be reused because there is no pin available for causing bending of the distal extremity of the guide tube assemblies 71 and 72.

From the foregoing construction it can be seen that the needle cartridge assembly 26 shown in FIGS. 1–12 has been constructed in a manner so that it is relatively simple and relatively inexpensive whereby it can be disposed of after a one-time use.

Another embodiment of an insulated needle electrode 281 which can be utilized in the guide tube assembly 71 and 72 is shown FIG. 13 and as shown therein consists of a needle electrode 282 formed of a suitable metal as for example a nickel titanium alloy or a flexible needle which can serve as a conductor that is provided with a pointed or sharpened tip 283. A fixed insulated sleeve 286 is coaxially disposed on the needle electrode 282 so as to leave a predetermined length of the electrode 282 exposed as for example a length of 7 millimeters. The insulating sleeve 286 can be formed in a suitable manner such as by dip-coating by immersing the same in a liquid insulating coating material and permitting the same to harden onto the exterior surface of the needle 282. Alternatively, the coaxial insulating layer 282 can be formed of a suitable heat shrinkable plastic which can serve as an insulating material. The insulating material can be formed of a suitable plastic material such as polyimide or Nylon.

In this embodiment of the invention it can be seen that the insulation is maintained in a fixed position with respect to the needle electrode 282. The distal extremity of insulation layer 286 can be tapered to provide a sharpened end 287 to aid the insulated needle electrode 282 to penetrate the urethral wall. In order to attempt to make temperature measurements in the manner hereinbefore described, a thermocouple 289 is embedded in the coaxial insulation 286 near the sharpened tip 287 as shown and is connected by conductors 289 which lead to the proximal extremity of the insulated needle electrode 281.

The use of the insulated needle electrode 281 is very similar to that hereinbefore described in connection with the needle electrodes hereinbefore described with exception that the needle electrode 281 will not be advanced out of the outer guide tube 74 until the distal extremity of the outer guide tube 74 is disposed in the appropriate position in the urethra after which the needle electrode 281 can be advanced and retracted to perform ablation procedures in the manner hereinbefore described with the coaxial insulation being disposed in the urethral wall to protect the urethral wall during ablation.

Another transurethral needle ablation device 301 is shown in FIGS. 14–21 incorporating another embodiment of the invention. As shown therein, it consists of a bridge assembly 302 which is adapted to have mounted thereon a removable sheath assembly 23 (not shown) of the type hereinbefore described and which has mounted therein a cystoscope or urethroscope 24 of a conventional type as hereinbefore described. A needle cartridge assembly 306 is removably mounted in the bridge assembly 302.

Figures 14, 17, 18, 19, 20, 21:
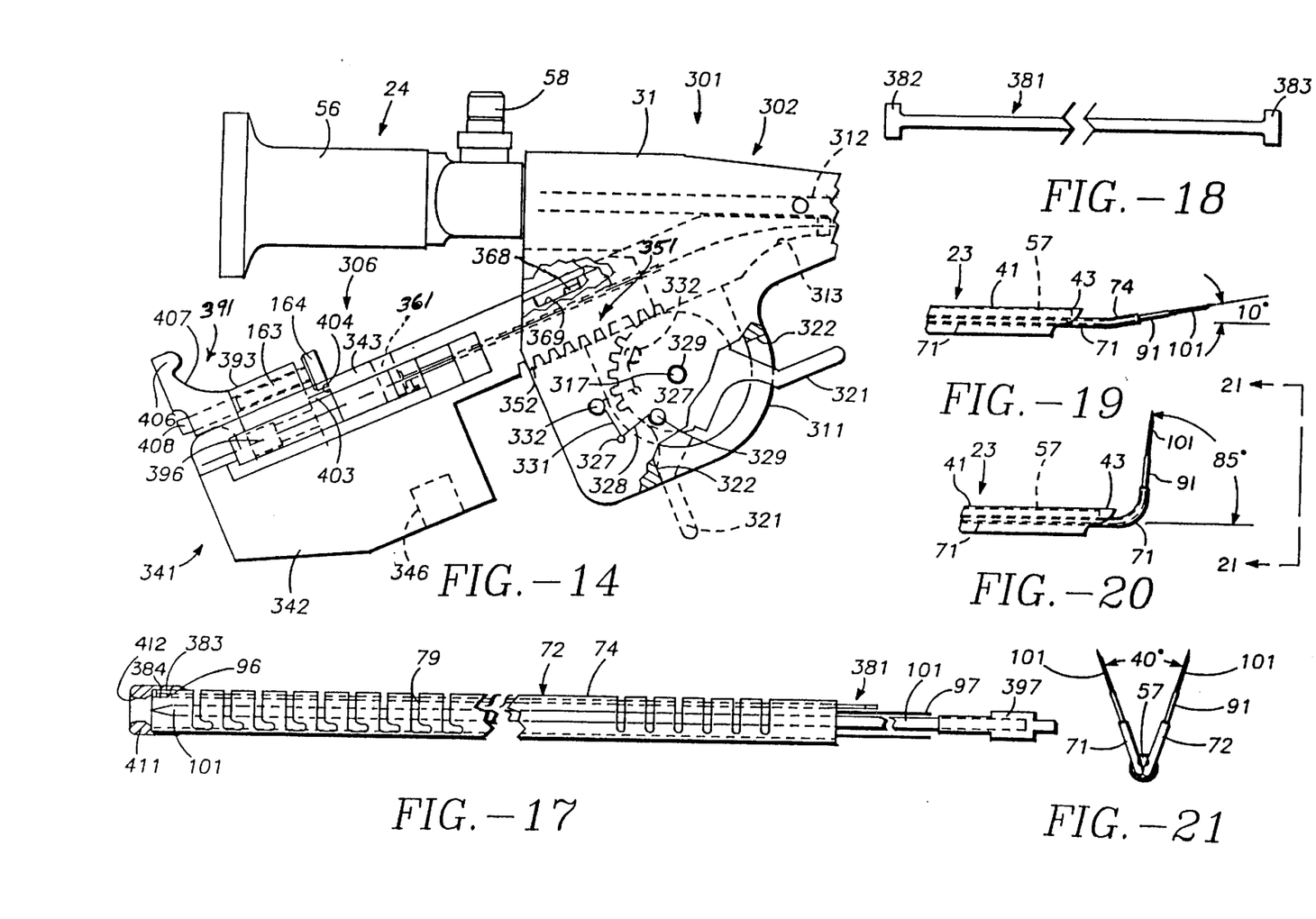
FIG. 14 is a side elevational view of the proximal portion of another embodiment of a transurethral needle ablation device incorporating the present invention.
FIG. 17 is an enlarged view of the distal extremity of the needle cartridge shown in FIG. 15.
FIG. 18 is a top plan view of the pull wire shown in FIG. 17.
FIG. 19 is a side elevational view of the distal extremity of the device shown in FIG. 14 with the needle assembly being deployed at an angle of 10°.
FIG. 20 is a view similar to FIG. 16 but showing the needle assembly being deployed at an angle of 85°.
FIG. 21 is an elevational view looking along the line 21—21 of FIG. 17.
Figure 15:
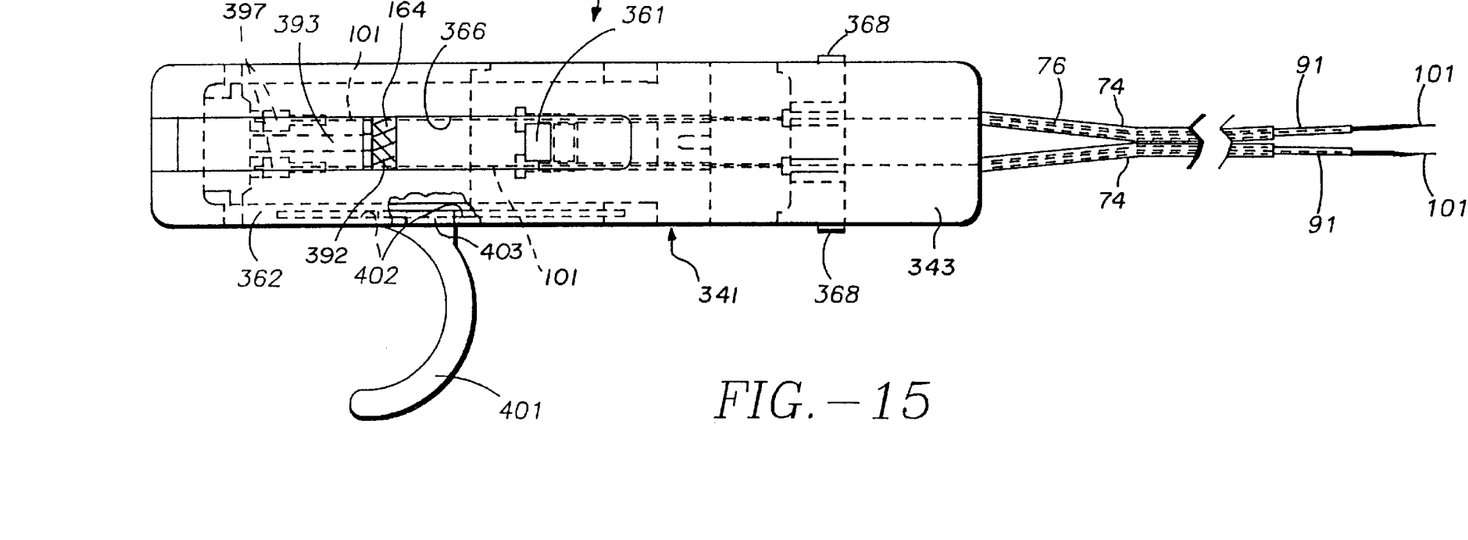
FIG. 15 is an enlarged top plan view of the needle cartridge of the device shown in FIG. 14.
Figure 16:
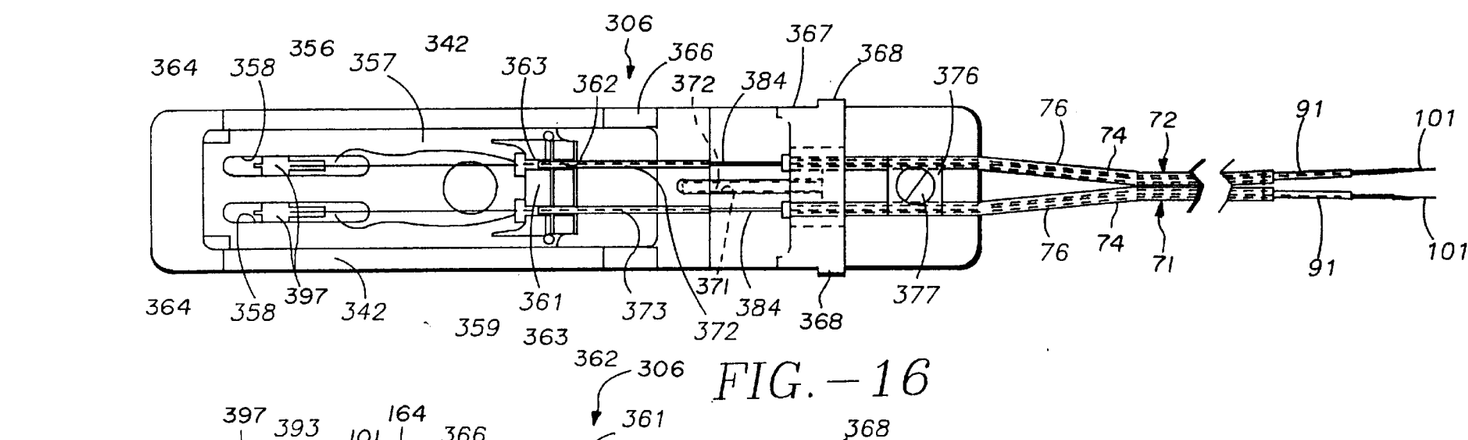
FIG. 16 is a view similar to that shown in FIG. 15 with the top cover plate and needle actuator removed.

The bridge assembly 302 consists of a bridge housing 311 similar to the bridge housing 31 hereinbefore described. The bridge housing 311 is formed of a suitable material such as a black polycarbonate. It is provided with a first passage 312 which is adapted to receive the cystoscope or urethroscope 24 as shown in FIG. 14. The passage 312 can be square in cross-section and overlies another passage 313 which can be oval-shaped in cross-section with the longest axis of the oval-shaped opening lying in a horizontal plane parallel to the passage 312.

The bridge assembly 302 includes a bridge gear 316 which includes an integral shaft 317 rotatably mounted in the bridge housing as shown. The gear 316 is generally cylindrical and is provided with a plurality of teeth 318 extending outwardly from the circumferential surface of the gear 316. The teeth 318 extend over a predetermined sector of the gear 316 as for example through an angle of 110° with two of the teeth 318 being removed after the first tooth as viewed in the most clockwise position in FIG. 14 to facilitate engagement with the needle cartridge assembly 306 as hereinafter described.

The gear 316 is provided with an outwardly extending handle 321 formed integral therewith which extends through an elongate arcuate slot 322 provided in the bridge housing 311 to permit movement of the handle 321 and the gear 316 carried thereby through a suitable angle as for example 90°. As hereinafter described, the handle 321 is utilized for moving the needle cartridge assembly 306 between an extreme forward position and a rearward position. The handle 321 is shown in solid lines in FIG. 14 with the needle cartridge assembly 306 in the rearmost position. The handle 321 is shown in dotted lines when the needle cartridge assembly 306 has been moved to an extreme forward position.

Toggle spring means is provided for retaining the handle 321 in either the forward or rearward positions and consists of a spring 326 formed from a single piece of spring wire which has an intermediate portion wound into two loops 327 and having one leg 328 engaging a pin 329 provided on the gear 316 and having another leg 331 engaging a pin 332 mounted in the bridge housing 311 (see FIG. 14). When the handle 321 is moved from the solid line position to the dotted-ine position 321 shown in FIG. 14, the toggle spring 326 toggles over center as shown in dotted lines in FIG. 14 to retain the handle 321 in the desired position.

The needle cartridge assembly 306 consists of a cartridge or housing 341 formed of a suitable material such as a black polycarbonate. The housing 341 consists of a body 342 and a cover plate 343. The cover plate 343 is secured to the body 342 by suitable means such as screws (not shown). A female electrical connector assembly 346 is mounted in the body 342 and can be of the type utilized in the telephone industry for making electrical connections.

The body 342 is provided with a rack 351 having a plurality of spaced-apart teeth 352 that are adapted to be engaged by the teeth 318 of the gear 316 of the bridge assembly 302. The third tooth 352 counting from the right as viewed in FIG. 14 is removed to make possible the mating of the needle cartridge assembly 306 with the bridge assembly 302 and to permit the teeth 318 of the gear 316 to mate with the teeth 352 of the rack 351 and thereafter to permit movement of the needle cartridge assembly 306 between its forwardmost and rearwardmost positions.

The body 342 of the cartridge housing 341 is provided with an upwardly facing rectangular recess 356 in which an insulation actuator 357 is slidably mounted for movement between first and second positions. The actuator 357 is provided with a pair of elongate slots 358 at the rearmost extremity thereof. It is also provided with a central viewing hole 359 forward of the slots 358 and an upwardly extending post 361. It is also provided with a pair of slots 362 extending on opposite sides of the post 361 which are adapted to receive the flanged proximity extremities of the insulation tubes 91. A pair of holes 363 are provided on opposite sides of the post 361 and are adapted to have the thermocouple wires 97 pass therethrough to be connected to the connector assembly 346. The insulation actuator 357 is provided with a pair of upstanding spaced-apart protrusions 364. The upstanding post 361 is positioned so that it can extend and travel in a slot 366 provided in the cover plate 343.

Another upwardly facing rectangular recess 366 is provided in the body 342 forward of the recess 356. A pull ribbon plate 367 formed of a suitable material such as stainless steel is slidably mounted in the recess 366 and is provided with ears 368 that protrude outwardly sidewise of the body 342 through elongate slots 369 provided on opposite sides of the cartridge housing 341. The plate 367 is provided with a longitudinally extending slot 371 which receives an upwardly extending protrusion 372 formed integral with the body 342 and extending upwardly into the recess 366. The slot 371 and the protrusion 372 cooperatively serve to guide the plate 367 between its forwardmost and rearwardmost positions within the recess 366.

The body 342 is provided with a pair of longitudinally extending slots 373 which underlie the plate 367 and which receive the insulation tubes 91 with the electrodes 101. The slots 373 extend proximally or rearwardly from the proximal extremities 76 of the outer guide tubes 74 and which are clamped into the front or distal extremity of the cartridge housing 341 by a plate 376 held in place by a screw 377 threaded into the body 342.

Each of the guide tube assemblies 71 and 72 is provided with a pull ribbon 381 which corresponds to the pull ribbons 86 hereinbefore described. The pull ribbon 381 as shown in FIG. 17 is in the form of an elongate stainless steel ribbon which is provided with T-shaped extremities 382 and 383. The pull ribbons 381 extend proximally from the proximal extremity 76 of the outer guide tubes 74 and extend through the slots 384 provided on opposite sides of the slot 371 in the plate 367 and have the T-shaped portions 382 engage an upstanding wall 386 formed on the plate 367. The insulation tubes 91 and the electrodes 101 along with the thermocouple wires 97 extend proximally with the insulation wires 97 passing through the holes 363 and with the flanged extremities of the insulation tubes 91 being fastened in the insulation actuator 357. The proximal extremities of the electrodes 101 extend proximally and are fastened into a needle actuator 391 formed of a suitable material such as a black carbonate. The needle actuator 391 is provided with a body 392 which is slidably mounted above the insulator actuator 357 and which has an upwardly extending protrusion 393 that extends through the slot 366 in the top cover plate 343. The body 392 is provided with bores 396. The distal extremities of the needle electrodes 101 are retained within the bores 396 by an adjustment screw insert 397 secured to the proximal extremity 102 of the needle electrodes 101 permitting the needle electrode 101 to be adjusted axially of the insulation tube 91 in which it is disposed.

A sidewise extending trigger handle 401 is formed integral with the body 392 of the needle actuator 391 and is configured to be engaged by the thumb of a human hand. The body 302 is provided with an inwardly extending recess 402 (see FIG. 16) to permit the handle 401 to be depressed inwardly by force of the thumb against the yieldable force of the plastic to cause an upwardly extending protrusion 403 to be pushed out of a slot 404 provided in the side of the top cover plate 343 so that the needle actuator 391 can be released and pushed forwardly or distally when desired.

Another upstanding handle 406 is provided as a part of the needle actuator 391 and is formed with a curved surface 407 to fit a finger of the human hand and is secured to the upstanding protrusion 403 by suitable means such as a screw 408. A needle adjustment screw 163 having a knob 164 of the type hereinbefore described is mounted in the upwardly extending protrusion 403.

In FIG. 17 there is shown the guide tube assembly 72. The pull ribbon 381 is mounted therein and has its distal tee-shaped portion 383 mounted in a slot 384 in the outer guide tube 74 just proximal of a nipple 411. The nipple 411 is formed of a suitable material such as stainless steel and is bonded to the distal extremity of the outer guide tube 74 by suitable means such as an adhesive. The nipple 411 is provided with a rounded forward extremity 412 as shown in FIG. 17 to provide a forward extremity for each of the guide tube assemblies 71 and 72 which can be readily guided through the urethra without damaging the urethra. As can be seen from FIG. 17, the needle electrode 101 during this movement is recessed a suitable amount as for example 0.010" to prevent the sharpened tip 103 of the needle electrode from engaging the urethral wall.

Operation and use of the embodiment of the transurethral needle ablation device 301 is very similar to that hereinbefore described. In using the device 301, the bridge 301 is utilized and a sheath assembly 23 of the type hereinbefore described is mounted on the sheath assembly. A cystoscope 24 is also mounted in the bridge 301 and in the sheath assembly 23 and extends through the sheath assembly 23. The removable needle cartridge assembly 306 is then taken and its distal extremity introduced into the bridge 301 through the passage 313 and into the sheath assembly 23. The knob 164 is adjusted to determine the amount that the needle electrode is to extend beyond the insulation tube 91 during an ablation procedure. The needle cartridge assembly 306 is connected to a control console 276 of the type hereinbefore described. The patient is prepared for the procedure in the manner hereinbefore described and the sheath 41 is introduced into the urethra and has its distal extremity disposed so that it lies in the urethra in the region within the patient's prostate surrounding the urethra. The device 301 is then rotated to the desired position within the urethra by using one hand. For example, it can be rotated so that the needle electrodes 101 will enter the median lobe of the prostate. The other hand grasps the handle 321 to cause rotational movement of the gear 316 to cause its teeth 318 to engage the teeth 352 of the rack 351 to cause advancement of the needle cartridge assembly 306 against the yieldable force of the toggle spring 326 to cause the distal extremities of the outer guide tubes 74 of the guide tube assemblies 71 and 72 to be advanced distally and at the same time to cause the distal extremities to be bent sidewise with respect to the longitudinal axis of the sheath 41 as tensioning forces are applied by the pull ribbon 381 as shown in FIG. 19. If, by way of example, it is desired to treat the median lobe of the prostate, a relatively small angle is utilized with respect to the longitudinal axis of the sheath 41, as for example an angle of 10° as shown in FIG. 18. As soon as the outer guide tubes 74 have been advanced sufficiently far and bent into the desired 10° angle, the handle 401 can be pressed inwardly to cause the protrusion 403 to be released from the slot 404. This permits the physician undertaking the procedure to have a finger of the hand engage the upstanding handle 406 and to advance the needle actuator 391 to first cause the needle electrode 101 to be advanced and thereafter as the adjustment knob 164 engages the upstanding post 361 to cause forward advancement of the insulation actuator 357. Thereafter the needle electrodes 101 and the insulation sleeves 91 are moved in unison as the handle 406 is pushed forwardly to cause the needle electrodes 101 and the insulation sleeves 91 carried thereby to penetrate the urethral wall with a minimum of tenting and thereafter enter the prostate with the needle electrodes 101 exposed a predetermined amount within the median lobe of the prostate and with the insulation tubes extending through the urethral wall. Radiofrequency ablation can thereafter be carried out in the manner hereinbefore described with the urethral wall being protected by the insulation sleeves 91.

When the ablation has been completed, the surface 407 of the handle 406 can be engaged by a finger of the hand and the needle actuator 391 retracted causing the needle electrodes 101 to be first retracted and followed by the insulation sleeves 91 when the needle actuator 391 engages the upstanding protrusions 364 provided on the insulator actuator 357 to cause the insulator actuator 357 to be thereafter retracted in unison to withdraw the needle electrodes 101 and insulation sleeves 91 into the confines of the outer guide tubes 74 so that the sharp tips 103 of the needle electrodes 101 are recessed in the outer guide tubes 74.

The device 301 can then be rotated into another location as desired by the physician as hereinbefore described. For example, it may be desired to perform radiofrequency ablation in one or both of the side or lateral lobes of the prostate in which it is desired to enter the prostate at substantially right angles, as for example of 85° with respect to the longitudinal axis of the sheath 43 as shown in FIG. 20. This can be readily accomplished in the manner hereinbefore described by operation of the handle 321 and moving it to the extreme dotted-line position shown in FIG. 14 to cause the distal extremity to be bent through the approximate 85° shown in FIG. 20. The needle electrodes 101 and insulation tubes 91 are then rapidly advanced through the urethral wall and into the prostate as hereinbefore described and thereafter radiofrequency ablation carried out.

As can be seen from FIG. 21, the distal extremities of the needle electrodes 101 are deployed sidewise from the longitudinal axis of the sheath 43 and typically subtend at an angle which is less than an acute angle, as for example 40° as shown in FIG. 21 during radiofrequency ablation. The distal extremities of the needles 101 as well as the distal extremities of the insulation tubes 91 can be observed by the cystoscope during positioning of the same.

The electrodes 101 and the insulation tubes 91 can be withdrawn in the manner hereinbefore described so that the distal extremities of the electrodes 101 are disposed within the outer guide tubes 74. The handle 321 can then be moved from the dotted-line position to the solid-line position going over center for the toggle spring 326 to cause the distal extremities of the guide tubes 74 to be straightened and to permit the same to be retracted into the sheath 43 after which the device 301 can be withdrawn from the urethra.

From the foregoing, it can be seen that in the additional embodiment of the device shown in FIGS. 14–21, there has been provided a device which is relatively simple in construction and which is relatively simple and foolproof to operate. Thus when the needle actuator 391 has been retracted to its rearmost position by engagement of the handle 306 and with the protrusions 403 snapping into the slots 404, the distal extremity of the needle 101 is retracted within the outer guide tubes 74 to prevent damage to the urethra of the patient during rotational movement and movement longitudinally in the urethra while prostatic ablation procedures are being performed in the patient.

What is claimed is:

1. A transurethral needle ablation device for use with the human hand for radio frequency ablation of a target volume in the tissue of a prostate of a human male having a bladder with a base and a penis with a urethra therein formed by a urethral wall extending into the base of the bladder along a longitudinal axis with the tissue of the prostate surrounding the urethra near the base of the bladder comprising a sheath having proximal and distal extremities and having a passageway therein, said sheath being sized so that it can enter the urethra and having a length so that when its distal extremity is in the vicinity of the prostate the proximal extremity is outside the urethra, a disposable needle assembly having proximal and distal extremities removably mounted in the passageway in the sheath, the needle assembly having proximal and distal extremities and including at least one needle electrode and an insulating sleeve coaxially disposed on the needle electrode, means carried by the proximal extremity of the needle assembly and the sheath for causing the distal extremity of the needle assembly to be moved sideways at an angle with respect to the longitudinal axis and for causing advancement of the at least one needle electrode and the insulation sleeve thereon through the urethral wall and into the target volume in the tissue of the prostate with a portion of the at least one needle electrode being free of the insulation but with the insulation extending through the urethral wall.

2. A device as in claim 1 wherein the needle assembly includes at least two needle electrodes and an insulating sleeve coaxially disposed on each of the needle electrodes and wherein the at least two needle electrodes extend at an angle less than an acute angle with respect to each other when they are disposed in the target volume.

3. A device as in claim 1 wherein the means carried by the proximal extremity of the needle assembly and the sheath for causing the distal extremity of the needle assembly to be moved sidewise at an angle with respect to the longitudinal axis includes means for selecting the angle of sidewise movement between 5° and 90°.

4. A device as in claim 3 wherein the angle is approximately 10°.

5. A device as in claim 3 wherein the angle is approximately 85°.

6. A device as in claim 1 together with an optical viewing device disposed in the passageway in the sheath to permit viewing of the distal extremity of said at least one needle electrode as it is moved sidewise.

7. A device as in claim 1 wherein said means for causing advancement of the at least one needle electrode includes means for rapidly advancing the at least one needle electrode through the urethral wall to minimize tinting of the urethral wall.

8. A device as in claim 1 together with means carried by the proximal extremity of the needle assembly for causing relative movement between the at least one needle electrode and the insulation thereon to adjust the length of the needle electrode exposed in the tissue of the prostate.

9. A device as in claim 8 wherein said means for adjusting relative positions of the at least one needle electrode and the insulation thereon can be preadjusted before the needle electrode is advanced through the urethral wall.

10. A device as in claim 1 together with temperature sensing means mounted on the insulating sleeve for measuring the temperature of the tissue of the prostate in the vicinity of the insulating sleeve.

11. A device as in claim 1 wherein said means carried by the proximal extremity of the needle assembly and the sheath includes a bridge and wherein said needle assembly includes a cartridge removably mounted in the bridge.

12. A device as in claim 1 wherein said means for causing advancement of the at least one needle electrode includes a yieldable member applying a yieldable force urging the needle electrode in a forward direction and a trigger mechanism for retaining said yieldable means in a predetermined position and including a trigger for releasing said yieldable means from said predetermined position to permit advancement of the at least one needle electrode under the force of the yieldable means.

13. A device as in claim 1 wherein said needle electrode is provided with a sharpened distal extremity and wherein said insulation sleeve is provided with a tapered distal extremity having a taper extending inwardly and forwardly.

14. A device as in claim 11 wherein the needle assembly includes an insulation actuator slidably mounted in the cartridge with the insulation sleeve secured thereto, a needle actuator slidably mounted on the insulation actuator and having a needle electrode secured thereto and cooperative means carried by the insulation actuator and the needle actuator for causing the insulation actuator to be advanced after the needle actuator has been advanced a predetermined amount and for causing retraction of the insulation actuator after the needle actuator has been retracted a predetermined amount.

15. A device as in claim 14 wherein said cooperative means includes means for adjusting the predetermined distance moved by the needle actuator prior to movement of the insulation actuator.

16. A device as in claim 14 wherein said cartridge and the insulation actuator and the needle actuator carried thereby are disposable after one-time use.

17. A device as in claim 1 wherein said cooperative mechanism includes means for adjusting the angle at which the needle electrode penetrates the urethral wall.

18. A device as in claim 7 together with optical viewing means for viewing the distal extremity of the at least one needle electrode as it penetrates the urethral wall to ascertain whether or not tenting of the urethral wall is taking place.

19. A device as in claim 1 together with means connected to the needle electrode for supplying radiofrequency energy to the needle electrode.

20. A device as in claim 19 together with temperature measuring means carried by the distal extremity of the insulation sleeve for measuring temperature during the time that radiofrequency ablation is taking place.

21. A method for the treatment of a prostate of a human male by the radio frequency ablation of a target volume in the tissue of the prostate of the human male having a bladder with a base and a penis with a urethra therein formed by a urethral wall extending into the base of the bladder along a longitudinal axis with the tissue of the prostate surrounding the urethra near the base of the bladder by the use of a disposable needle assembly having proximal and distal extremities comprising advancing the distal extremity of the needle assembly into the vicinity of the prostate, causing bending of the distal extremity of the needle assembly so that the distal extremity extends in a direction which is substantially at an angle to the longitudinal axis and rapidly advancing the needle electrode through the urethral wall and into the tissue of the prostate to minimize tenting of the urethral wall during the time that the needle electrode is passing through the urethral wall.

* * * * *